(12) United States Patent
Manenti et al.

(10) Patent No.: US 7,662,800 B2
(45) Date of Patent: Feb. 16, 2010

(54) HYALURONIC ACID DERIVATIVES

(75) Inventors: Demetrio Manenti, Milan (IT); Gaspare Aita, Milan (IT)

(73) Assignee: Jasper Ltd. Liability Co., Cheyenne, WY (US)

( * ) Notice: Subject to any disclaimer, the term of this patent is extended or adjusted under 35 U.S.C. 154(b) by 315 days.

(21) Appl. No.: 10/522,602

(22) PCT Filed: Jul. 24, 2003

(86) PCT No.: PCT/IB03/02946

§ 371 (c)(1),
(2), (4) Date: Mar. 17, 2005

(87) PCT Pub. No.: WO2004/013182

PCT Pub. Date: Feb. 12, 2004

(65) Prior Publication Data

US 2005/0239727 A1 Oct. 27, 2005

(30) Foreign Application Priority Data

Jul. 26, 2002 (IT) .......................... MI2002A1666

(51) Int. Cl.
*A61K 31/728* (2006.01)
*A61K 31/715* (2006.01)
(52) U.S. Cl. ...................... 514/54; 514/256; 514/263.1; 536/123.1; 536/124
(58) Field of Classification Search ................... 514/54, 514/256, 263.1; 536/123.1, 124
See application file for complete search history.

(56) References Cited

FOREIGN PATENT DOCUMENTS

| EP | 0 555 898 A | * | 8/1993 |
|---|---|---|---|
| EP | 0 555 898 A2 | | 8/1993 |
| WO | 00/01733 | | 1/2000 |
| WO | WO 00 01733 | * | 1/2000 |

OTHER PUBLICATIONS

International Search Report.
Adenine—definition of adenine arabinoside in the Medical Dictionary, retrieved from http://medical-dictionary.thefreedictionary.com/p/adenine on Sep. 25, 2008.
Arabinose—article about arabinose from Wikipedia Encyclopedia, retrieved from http://encyclopedia.thefreedictionary.com/p/arabinose on Sep. 25, 2008.
Nucleobase—article about nucleobase from Wikipedia Encyclopedia, retrieved from http://encyclopedia.thefreedictionary.com/p/nucleobase on Sep. 25, 2008.
Ribose—article about ribose from Wikipedia Encyclopedia, retrieved from http://encyclopedia.thefreedictionary.com/p/ribose on Sep. 25, 2008.
Vidarabine—article about vidarabine from Wikipedia Encyclopedia, retrieved from http://encyclopedia.thefreedictionary.com/p/vidarabine on Sep. 25, 2008.

* cited by examiner

*Primary Examiner*—Shaojia Anna Jiang
*Assistant Examiner*—Michael C Henry
(74) *Attorney, Agent, or Firm*—Nixon & Vanderhye P.C.

(57) ABSTRACT

Derivatives between hyaluronic acid and at least one nitrogenated base, in particular at least one heterocyclic compound derived from purine and/or from pyrimidine and cosmetic and/or pharmaceutical compositions based on said derivatives.

27 Claims, No Drawings

HYALURONIC ACID DERIVATIVES

This application is the US national phase of international application PCT/IB2003/002946 filed 24 Jul. 2003 which designated the U.S. and claims benefit of IT MI2002A001666, dated 26 Jul. 2002, the entire content of which is hereby incorporated by reference.

SUBJECT OF THE INVENTION

The subject of the present invention are new derivatives of hyaluronic acid, a process for the preparation of said derivatives, their use in the cosmetic and/or pharmaceutical field, and the cosmetic and/or pharmaceutical compositions that comprise them.

STATE OF THE ART

Hyaluronic acid is a mucopolysaccharide present practically in every part of the living organism and in particular in the dermis. Chemically, hyaluronic acid is made up of linear polymeric chains which have a molecular weight of hundreds of thousands to millions of dalton, in which disaccharide units consisting of N-acetylglucosamine and glucoronic acid, bonded together by glucoside bonds, are repeated. Hyaluronic acid possesses the capacity for bonding considerable amounts of water coming from the capillary network, necessary for maintaining in solution the catabolytes, the electrolytes and the gases that are diffused from the capillaries to the cells and vice versa, through the interstitial liquid. Hyaluronic acid thus performs a fundamental role in controlling the diffusion of nutritive substances, hormones, vitamins and inorganic salts of the connective tissue and in removing the metabolic detritus that may give rise to reactions of an inflammatory type. Thanks to the characteristics indicated above, hyaluronic acid is very much exploited in cosmetic preparations, for example for restoring proper hydration of the tissues and thus counteracting the processes of ageing of the tissues, in particular of the skin. There have been known for some time derivatives of hyaluronic acid obtained by means of formation of covalent bonds between hyaluronic acid and other compounds. For example, there are known amides of hyaluronic acid, to obtain which there is formed a covalent bond between the carboxyl group of hyaluronic acid and an amine group present on the reagent. These amide derivatives are prepared, for example, by means of activation of the carboxyl group (for example, by transformation of the same in an activated ester) and subsequent reaction with the amine group of the reagent. The reaction envisages the formation of a new covalent bond and the elimination of a molecule of water (or, for example, of hydrochloric acid in the case where the ester is activated) for each amide bond that is formed. There are also known esters of hyaluronic acid, where the carboxyl group (possibly activated in an appropriate way) has reacted with an hydroxyl derivative to form a new bond of a covalent type (ester), with elimination, also in this case, of a molecule of water (or acid) for each bond of an ester type obtained. All these derivatives have in common the characteristic of proving extremely stable compounds and in particular resistant to enzymatic attack, so as to be able to guarantee, if administered, a greater resistance and duration of their effect over time.

OBJECTS OF THE INVENTION

An object of the present invention is to provide derivatives of hyaluronic acid that will be provided with bonds that are labile and readily hydrolysable in mild conditions, also by enzymatic effect.

A further object of the present invention is to make available derivatives of hyaluronic acid which are characterized by high efficacy in the cosmetic and pharmaceutical field and which have chemical-physical characteristics such as to enable use thereof in a wide range of types of formulations.

Yet another object of the present invention is to make available cosmetic and/or pharmaceutical compositions with a base of derivatives of hyaluronic acid, and a process for their preparation.

DESCRIPTION

The above and yet other purposes and corresponding advantages, which will be clarified in greater detail in what follows, are achieved by derivatives between hyaluronic acid and at least one nitrogenated base, in particular at least one heterocyclic compound derived from purine and/or from pyrimidine.

According to the invention, said hyaluronic acid is hyaluronic acid with high molecular weight, said molecular weight being comprised in a range between 400 000 and 4 million dalton, preferably between 800 000 and 3.5 million dalton, and in particular between 1.5 and 3 million dalton.

Always according to the invention, said hyaluronic acid is hyaluronic acid with low molecular weight, said molecular weight being, for example, comprised in a range between 80 000 and 400 000 dalton.

According to the present invention, said derivatives of purine are chosen between adenine and/or guanine, while said derivatives of pyrimidine are chosen between thymine and cytosine. The aforesaid derivatives of purine and of pyrimidine are commonly referred to by the term "purine and pyrimidine bases". Once again according to the invention, other derivatives of purine and pyrimidine, commonly referred to by the term "minor bases", which may advantageously yield derivatives with hyaluronic acid, are the following:

5,6 dihydrouracyl
1-methyluracyl
3-methyluracyl
5-hydroxymethyluracyl
2-thiouracyl
$N^4$-acetylcytosine
3-methylcytosine
5-methylcytosine
5-hydroxymethylcytosine
1-methyladenine
2-methyladenine
7-methyladenine
$N^6$-methyladenine
$N^6,N^6$-dimethyladenine
$N^6$-($\Delta^2$-isopentenyl)adenine
1-methylguanine
7-methylguanine
$N^2$-methylguanine
$N^2,N^2$-dimethylguanine.

In practice, according to the present invention, hyaluronic acid is made to react with at least one purine and/or pyrimidine base chosen between the ones indicated above, in reaction conditions such as to form at least one bond of a ionic type between at least one "acid" centre of hyaluronic acid, such as for example a free carboxyl group in the form of an acid or in the form of a carboxylate salt, and at least one basic centre of the purine and/or pyrimidine base, which is also in the form of a free base or of an ammonium salt. The reaction scheme may in general be indicated as follows:

SCHEME 1

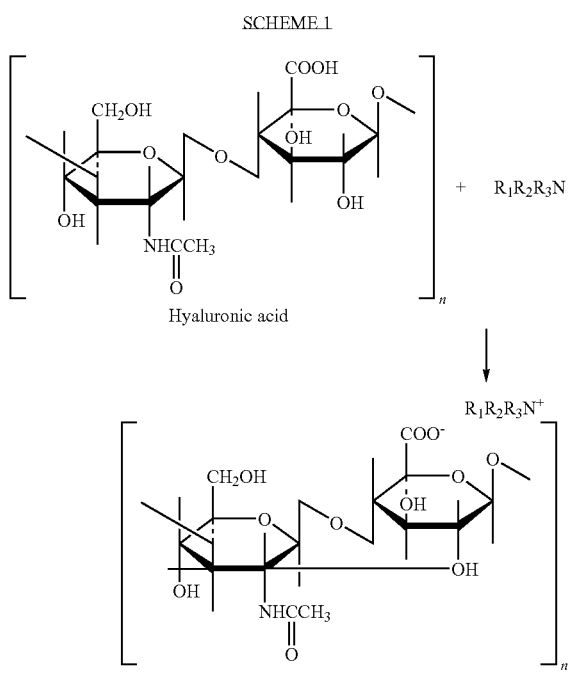

Where $R_1R_2R_3N$ indicates generically at least one purine or pyrimidine base. The bases most commonly used have the following formulae:

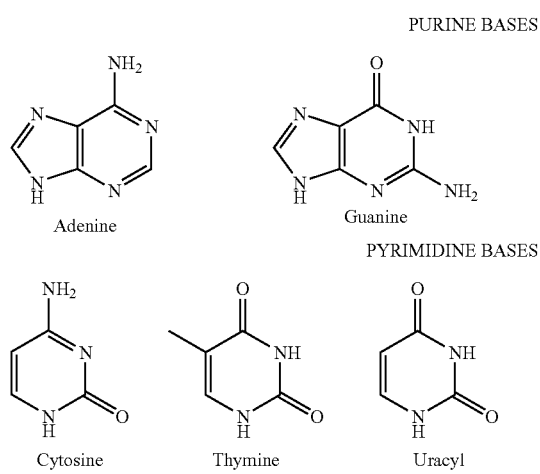

An important characteristic of purine and pyrimidine bases is their capacity of forming hydrogen bonds by means of the —$NH_2$ groups where available, the —NH-groups and the markedly electronegative atoms of oxygen. At least one amine group characteristic of the bases referred to above, both just as they are and in the form of a salt, reacts with at least one carboxyl group of hyaluronic acid, (which is also just as it is in appropriate reaction conditions or in the form of a carboxylate salt) to yield a salt, characterized by the formation of at least one bond of a ionic type between the carboxyl group and the amine group. Always according to the present invention, by varying the reaction ratios between hyaluronic acid and the purine/pyrimidine bases, as well as by using bases different from one another for subsequent stages of salification, it is possible to prepare mixed salts between a number of purine/pyrimidine bases so as to obtain a "cocktail" with specific characteristics suitable for the different applications.

Hyaluronic acid salified with at least one purine/pyrimidine base is characterized by a viscosity on average lower than that of the derivatives of hyaluronic acid according to the known art, characterized in that they are obtained by means of formation of covalent bonds. The derivatives of hyaluronic acid according to the present invention are thus characterized by a lower stability and duration in time as compared to those according to the known art, and this constitutes an advantage because they are able to make available hyaluronic acid just as it is, or other products or active principles linked thereto, rapidly after administration in that they undergo rapid hydrolysis of the ionic bond (or ionic bonds) that characterize them.

There appear hereinafter some examples of practical embodiment provided purely by way of indicative and non-limiting examples of the present invention.

Example 1

Reaction Between Guanine and Hyaluronic Acid to Obtain Guanine Hyaluronate (I)

1 g of sodium hyaluronate is made to react with 0.467 g of guanine hydrochlorate.

The preparation of the product takes place according to the following steps:

a) preparation of sodium hyaluronate gel by mixing sodium hyaluronate with water;

b) addition of guanine hydrochloride to the sodium hyaluronate gel;

c) lyophilization of the product.

There are suspended under stirring 10 g of sodium hyaluronate in 300 ml of deionized water, up to complete gelification. The product appears clear, colourless, homogeneous and without clots.

The hyaluronic acid/water ratios are purely indicative; in the case where it is not intended to proceed to drying or lyophilization of the product and it is intended to use the gel directly, there may be used larger amounts of water (both at the start and at the end of the reaction) in order to obtain a product with more appropriate physical characteristics (for example, viscosity). To the sodium hyaluronate gel previously prepared, there are then added slowly and under stirring 250 ml of solution containing 0.467 g of guanine hydrochloride. At the end of the addition, the product is kept under stirring for approximately 1 hour to obtain complete homogenization thereof. In the case where it is desired to modify the pH of the product, an acid or a base is added under the control of a pHmeter until the desired pH is reached.

The product obtained is kept in a refrigerator for 12 hours and then undergoes lyophilization or drying in vacuum conditions. A variation to the method described above consists in adding the hyaluronate gel to the solution of guanine hydrochloride.

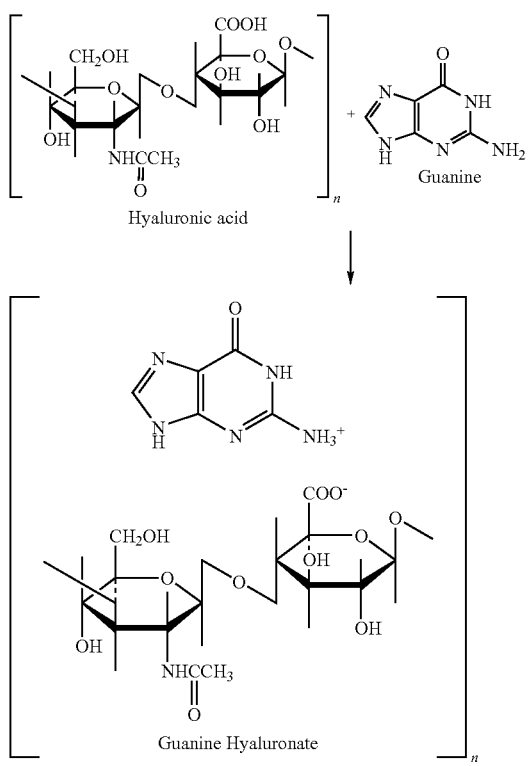

Hyaluronic acid + Guanine

↓

Guanine Hyaluronate

To the product obtained according to the example referred to above, there may be associated other and different organic molecules that are co-ordinated thereto by means of hydrogen bonds.

Example 2

Reaction Between Adenine and Hyaluronic Acid to Obtain Adenine Hyaluronate (II)

1 g of sodium hyaluronate is made to react with 0.450 g of adenine hydrochloride hemihydrate.

The preparation of the product takes place according to the following steps:
a) preparation of the gel by mixing sodium hyaluronate with water;
b) addition of adenine hydrochloride hemihydrate to the sodium hyaluronate gel;
c) lyophilization of the product.

There are suspended, under stirring, 10 g of sodium hyaluronate in 300 ml of deionized water, up to complete gelification. The product appears clear, colourless, homogeneous and without clots. The hyaluronic acid/water ratios are only indicative. In the case where it is not intended to proceed to drying or lyophilization of the product, and it is intended to use the gel directly, it is possible to use larger amounts of water (both at the start and at the end of the reaction) in order to obtain a product with the most appropriate physical characteristics (for example viscosity).

To the sodium hyaluronate gel previously prepared, there are added slowly and under stirring 250 ml of solution containing 4.45 g of adenine hydrochlorate hemihydrate. At the end of the addition the product is kept under stirring for approximately 1 hour to obtain the complete homogenization thereof. In the case where it is desired to modify the pH of the product, an acid or a base is added under control of a pHmeter until the desired pH is reached. The product is left resting in a refrigerator for 12 hours, and this is followed by lyophilization or drying of the product in vacuum conditions.

A variation to the method indicated consists in adding the hyaluronate gel to the solution of adenine hydrochloride.

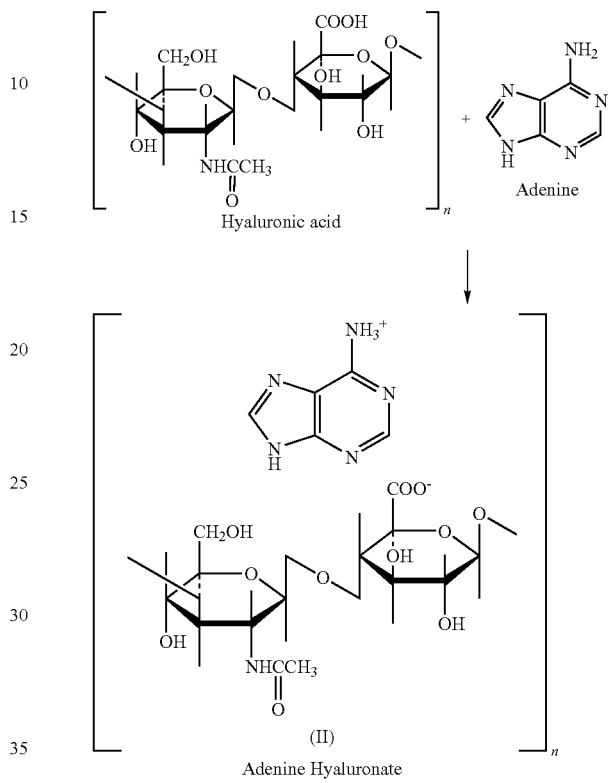

Hyaluronic acid + Adenine

↓

Adenine Hyaluronate (II)

To the adenine hyaluronate derivative (II) obtained as described above it is possible to associate other and different organic molecules that are co-ordinated thereto by means of hydrogen bonds.

Natural amino acids, their oligomers and their polymers (peptides) can react with the derivatives of hyaluronic acid according to the invention (hyaluronic acid salified with at least one purine/pyrimidine base) to yield further products of salification with possible free carboxyl groups that are still present. In practice, if the aim is to schematize the reaction, and indicating the reagents as HA (hyaluronic acid), BP (purine/pyrimidine bases), and NA (natural amino acids, their oligomers and their polymers), we shall obtain the following scheme:

Scheme 2

$(HA)_n + (BP)_{n-1} = (HA)_n (BP)_{n-1}$ $(HA)_n (BP)_{n-1} + NA = (HA)_n (BP)_{n-1} (NA)$

For example, if guanine hyaluronate (I) or adenine hyaluronate (II) as described in the foregoing examples is obtained using a base deficiency with respect to hyaluronic acid, these can react in appropriate conditions with one or more natural amino acids and/or their oligomers and/or their polymers (peptides) to obtain further salts of hyaluronic acid that will be characterized, as well as by the presence of at least one purine/pyrimidine base, also by the presence of at least one natural amino acid or its oligomer or polymer. The characteristics of the final product will thus include both those of hyaluronic acid and those of the purine bases and of the amino acids, since also in this case the bond that is formed is of a ionic type with high ease of hydrolysis and hence the corresponding availability of the species just as they are.

Example 3

Reaction Between Adenine Hyaluronate (II) and Polylysine 1 g of adenine hyaluronate (salified at 50% with adenine) is made to react with 0.143 g of polylysine. The preparation of the product takes place according to the following steps:
a) preparation of the gel by mixing hyaluronic acid with water/Adenine;
b) addition of the polylysine to the hyaluronic-acid gel/Adenine (compound II);
c) lyophilization of the product.

There are suspended under stirring 10 g of hyaluronic acid in 300 ml of deionized water, up to complete gelification. The product appears clear, colourless, homogeneous and without clots. The gel obtained has a pH of 6.6.

The hyaluronic acid/water ratios are indicative. In the case where it is not intended to proceed to drying or lyophilization of the product and it is intended to use the gel directly, it is possible to use larger amounts of water (both at the start and at the end of the reaction) in order to obtain a product with the most appropriate physical characteristics (for example viscosity). To the hyaluronic-acid/Adenine gel previously prepared (Compound II) there are added slowly and under stirring 200 ml of a solution containing 1.51 g of polylysine. At the end of the addition, the product is kept under stirring for approximately 1 hour to obtain complete homogenization thereof. In the case where it is desired to modify the pH of the product, an acid or a base is added under the control of a pHmeter until the desired pH is reached. The product is left resting in a refrigerator for 12 hours, and this is followed by lyophilization or drying of the product in vacuum conditions.

A variation to the method indicated consists in adding the hyaluronic-acid/Adenine (Compound II) to the solution of polylysine.

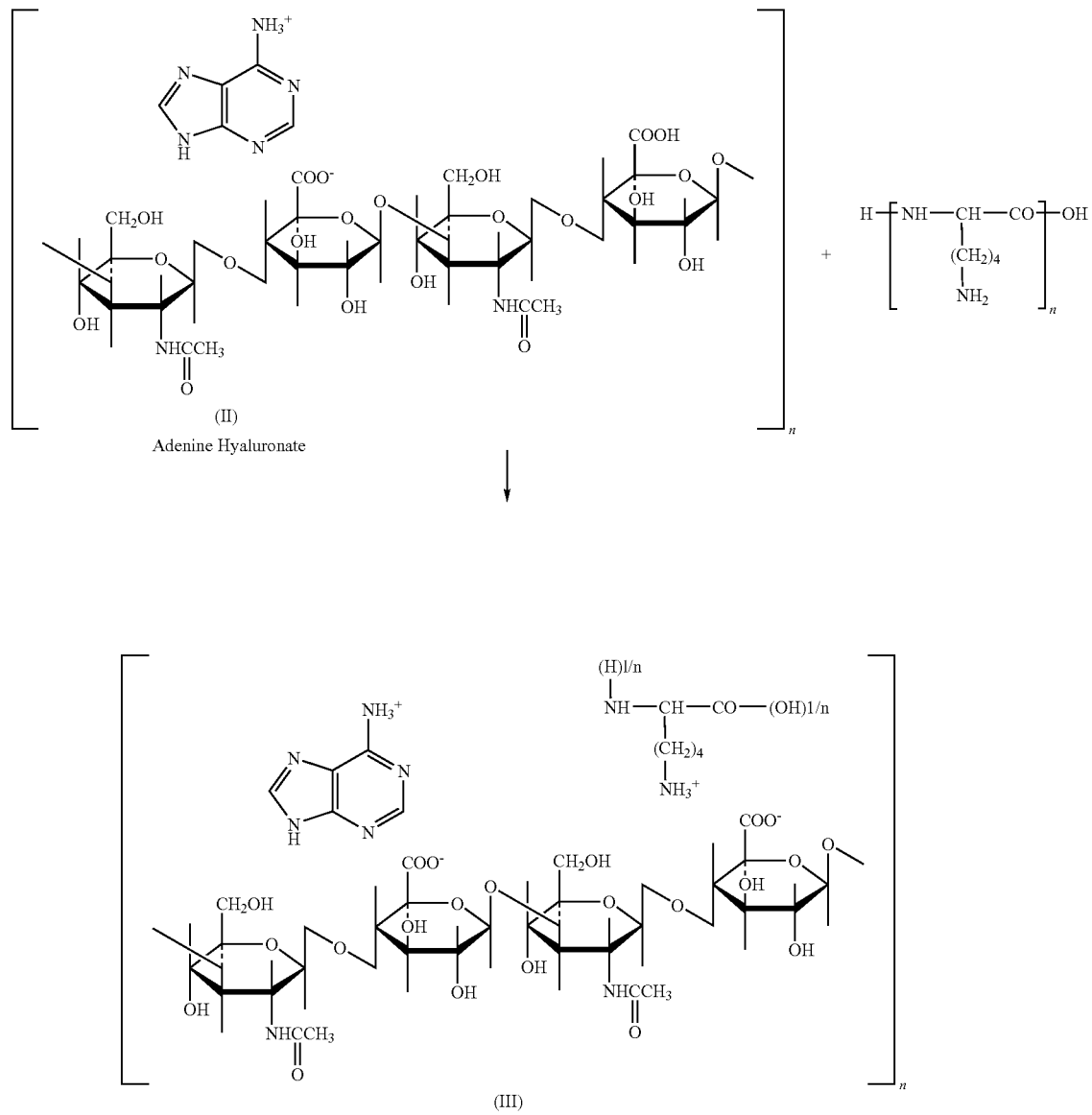

To the product obtained it is possible to associate other and different organic molecules that are co-ordinated thereto by means of hydrogen bonds.

As regards the product (III), as emerges from the scheme referred to above, it is understood that the unit deriving from the polylysine will be present n times according to the molar ratios between the reagents.

In the same way, the guanine hyaluronate (I) may react with polylysine or other oligomers or polymers (peptides) of amino acids.

Example 4

Reaction Between Guanine Hyaluronate (I) and

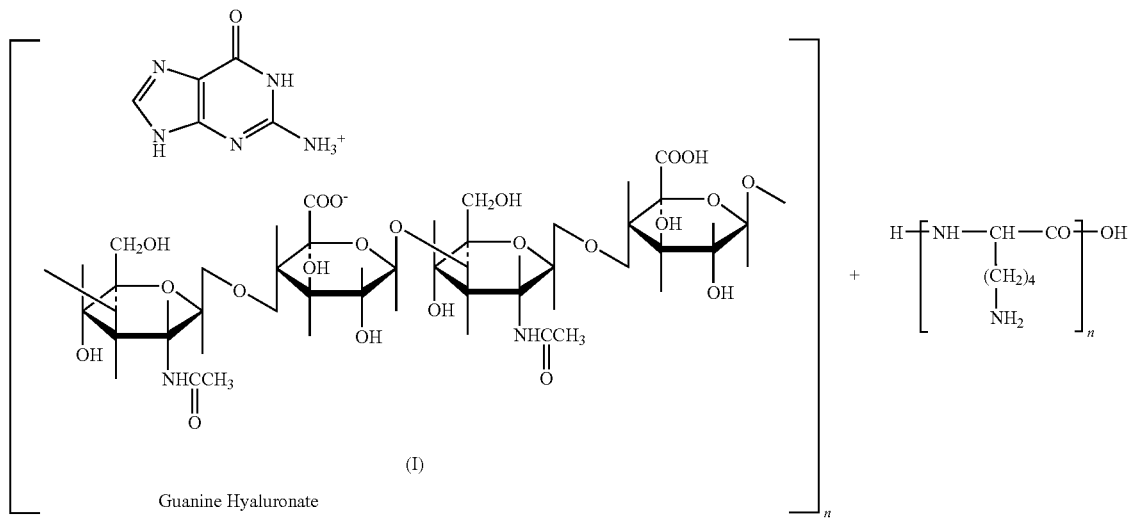

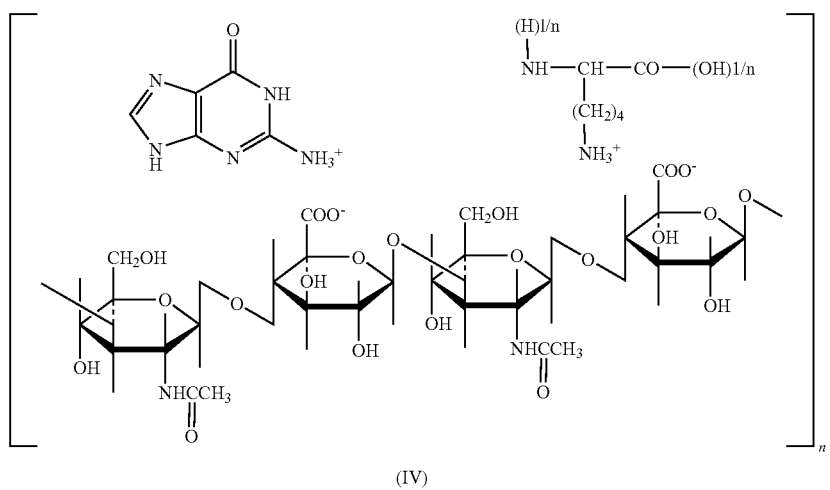

Also in this case, as regards the product (IV) as emerges from the scheme appearing above, it is understood that the unit deriving from the polylysine will be present n times according to the molar ratios between the reagents.

The reactions of the derivatives forming the subject of the present invention may be conducted using, as has already been said, stoichiometric amounts of the reagents or an excess of one of the components. By stoichiometric amounts of the reagents it is meant that the number of moles of basic compound used is equal to the number of the carboxyl functions present in hyaluronic acid. The possibility of varying the ratio between moles of acid and moles of base enables modulation of the characteristics of the products that can be obtained according to the properties desired.

The derivatives between hyaluronic acid and purine/pyrimidine bases according to the present invention may react also with other compounds that will be able to form bonds of an ionic type with the possible residual carboxyl groups present on hyaluronic acid. For example, there may be used, for further salification of derivatives of hyaluronic acid, modified amino acids, polyamino acids, growth factors, active principles with pharmacological activity, angiogenesis inhibitor factors, etc.

In each of the cases described above, the possibility of rapidly hydrolysing the ionic bond between the aforesaid compounds and hyaluronic acid, which is in turn salified with at least one purine/pyrimidine base, makes the product immediately available just as it is, but enables its vehicling and delivery to the "target" identified with equal rapidity, thanks to the considerable ease of diffusion of the derivatives of hyaluronic acid according to the invention.

The reaction of salification between hyaluronic acid and purine/pyrimidine base may occur by means of reaction between an acid and a free base, or else between an acid in the form of salt (carboxylate) and a base also salified with organic and/or inorganic acids. In this latter case, the reaction envisages an ion exchange so as to obtain the desired product in appropriate conditions. The reaction may be conducted using stoichiometric amounts of reagents or an excess of one of the two components, in which case the salt and a co-ordination of the reagent in excess is obtained by means of the formation of hydrogen bonds. In this way it is possible to modulate the characteristics of the hyaluronate derivatives (hyaluronic acid and purine/pyrimidine base) and possibly of further active principles or other components associated thereto, as described above. Said active principles or other components may be associated to the hyaluronate derivatives by co-ordination by means of the formation of hydrogen bonds. To the product obtained it is possible to add both organic and inorganic acids or bases (for example, glucosamine and glucuronic acid), with the purpose of modifying its pH and possibly its pharmacological activity, if present.

Yet again according to the present invention, hyaluronic acid may be cross-linked by means of formation of bonds of a covalent type (breaking of a preceding bond of a covalent type and formation of a new bond once again of a covalent type) between side chains. In particular, in the cross-linking reaction there may be involved both hydroxyl groups (OH) and carboxyl groups (COOH) present on the molecule of hyaluronic acid.

For example, in the case of the cross-linking reaction by means of esterification of the hydroxyl groups, this takes place rapidly even at room temperature using chlorides of organic acids according to the following scheme:

ClOCR'COCl+2ROH→RO—OCR'CO—OR+2HCl where ROH represents hyaluronic acid. The reaction may, for example, be conducted in an inert solvent such as chlorobenzole or in a solvent such as DMF, which neutralises the hydrochloric acid produced by the reaction. The reaction may be performed on free hyaluronic acid or on its inorganic salt or organic salt thereof.

Likewise, the cross-linking reaction by means of esterification of the carboxyl groups, envisages for example the use of chloro-organic compounds, which react with the carboxyl groups of hyaluronic acid according to the following scheme:

Cl—R'—Cl+2RCOOH→RCOO—R'—OCOR+2HCl

Where RCOOH represents hyaluronic acid. The reaction may be performed on free hyaluronic acid, an inorganic salt thereof (in this case, instead of HCl, the corresponding hydrochloride salt is obtained) or an organic salt.

Example 5

Cross-Linking by Esterification with Phosgene

An aqueous solution of sodium hyaluronate (1 g in 500 ml of water) is prepared.

There is then prepared a solution of $COCl_2$ (phosgene) 0.01 g-0.005 g in 20-50 ml of chloroform. The amount of phosgene given is simply indicative and may vary according to the degree of cross-linking desired. The solution of chloroform is added to that of sodium hyaluronate under stirring, thus obtaining the cross-linking. If the reaction is conducted in the absence of stirring, keeping the two phases (water and chloroform) in contact, in the interface there is formed a film of cross-linked polymer that may be removed continuously. The reaction takes place rapidly at room temperature.

According to a preferred aspect of the present invention, the derivatives of hyaluronic acid according to the invention are used as active principles in the preparation of medicaments. They are suitable for being formulated with appropriate excipients, for example those generally used in the cosmetic field, such as beeswax, jojoba oil, isostearyl isosterate, fatty acids, triglycerides, propylene glycol, laurilic alcohol and hydroxypropyl methylcellulose. There may moreover be added to these stabilizing active principles, antioxidants and preservatives, either alone or in combination with one another. As stabilizing agents butylhydroxyanisole, citric acid, tocorpherol, or sodium thiophosphate may be used. As preservatives, esters of p-hydroxybenzoic acid or imidazolidinurea may be used.

The invention claimed is:

1. A derivative formed between hyaluronic acid and at least one heterocyclic compound selected from the group consisting of guanine, thymine, cytosine, uracil, 5,6 dihydrouracil, 1-methyluracil, 3-methyluracil, 5-hydroxymethyluracil, 2-thiouracil, $N^4$-acetylcytosine, 3-methylcytosine, 5-methylcytosine, 5-hydroxymethylcytosine, 1-methylguanine, 7-methylguanine, $N^2$-methylguanine, and $N^2,N^2$-dimethylguanine; said derivative having at least one ionic bond between said hyaluronic acid and said at least one heterocyclic compound.

2. The derivative according to claim 1, characterized in that said hyaluronic acid is hyaluronic acid of high molecular weight.

3. The derivative according to claim 2, characterized in that said hyaluronic acid has a molecular weight of between 400 000 and 4 million dalton.

4. The derivative according to claim 3, characterized in that said hyaluronic acid has a molecular weight of between 800 000 and 3.5 million dalton.

5. The derivative according to claim 4, characterized in that said hyaluronic acid has a molecular weight of between 1.5 and 3 million dalton.

6. The derivative according to claim 1, characterized in that said hyaluronic acid is hyaluronic acid of low molecular weight.

7. A derivative formed between hyaluronic acid and at least one heterocyclic compound selected from the group consisting of guanine, thymine, and cytosine; said derivative having at least one ionic bond between said hyaluronic acid and said at least one heterocyclic compound.

8. The derivative according to claim 1, characterized in that said ionic bond is obtained between said hyaluronic acid and at least two of said heterocyclic compounds that are the same as or different from one another.

9. The derivative according to claim 7, characterized in that it is guanine hyaluronate.

10. The derivative according to claim 1, further comprising at least one organic compound selected from the group consisting of natural amino acids, their oligomers, and their polymers.

11. The derivative according to claim 9 further comprising at least one organic compound selected from the group consisting of natural amino acids, their oligomers and their polymers.

12. The derivative according to claim 9 further comprising polylysine, characterized in that it is guanine hyaluronate, polylysine.

13. A derivative having at least one ionic bond between hyaluronic acid and adenine, and further comprising polylysine, characterized in that it is adenine hyaluronate, polylysine.

14. The derivative according to claim 1, characterized in that it is cross-linked.

15. The derivative according to claim 14, characterized in that said cross-linking involves at least one hydroxyl group and/or at least one carboxyl group present on said hyaluronic acid.

16. The derivative according to claim 14, characterized in that said cross-linking is obtained with phosgene.

17. A process for the preparation of a derivative formed between hyaluronic acid and at least one heterocyclic compound referred to in claim 1, the process comprising reacting at least one carboxyl group of the hyaluronic acid or a salt thereof with at least one amine group of the heterocyclic compound in free or salified form to form at least one ionic bond.

18. A process for the preparation of a derivative formed between hyaluronic acid and at least one heterocyclic compound referred to in claim 1, which further comprises at least one organic compound selected from the group consisting of natural amino acids, their oligomers, and their polymers, the process comprising reacting said derivative or a salt thereof with said at least one organic compound in free or salified form.

19. A cosmetic or pharmaceutical composition comprising said derivative having at least one ionic bond between said hyaluronic acid and said at least one heterocyclic compound referred to in claim 1.

20. A cosmetic or pharmaceutical composition comprising said derivative having at least one ionic bond between said hyaluronic acid and said at least one heterocyclic compound, and further comprising at least one organic compound referred to in claim 10.

21. The derivative according to claim 10, characterized in that said organic compound is a peptide.

22. The derivative according to claim 11, characterized in that said organic compound is a peptide.

23. The derivative according to claim 7 further comprising at least one organic compound selected from the group consisting of natural amino acids, their oligomers, and their polymers.

24. The derivative according to claim 23, characterized in that said organic compound is a peptide.

25. The derivative according to claim 7, characterized in that it is cross-linked.

26. The derivative according to claim 25, characterized in that said cross-linking involves at least one hydroxyl group and/or at least one carboxyl group present on said hyaluronic acid.

27. The derivative according to claim 25, characterized in that said cross-linking is obtained with phosgene.

* * * * *